United States Patent [19]
Chu et al.

[11] Patent Number: 6,051,003
[45] Date of Patent: *Apr. 18, 2000

[54] COMBINED MULTIPLE LIGATING BAND DISPENSER AND SCLEROTHERAPY NEEDLE INSTRUMENT

[75] Inventors: Michael S. H. Chu, Brookline; Yem Chin, Burlington, both of Mass.

[73] Assignee: Boston Scientific Corporation, Natick, Mass.

[ * ] Notice: This patent is subject to a terminal disclaimer.

[21] Appl. No.: 08/968,352

[22] Filed: Nov. 12, 1997

Related U.S. Application Data

[63] Continuation of application No. 08/324,132, Oct. 14, 1994, Pat. No. 5,697,940, and a continuation-in-part of application No. 07/960,081, Oct. 9, 1992, Pat. No. 5,269,789.

[51] Int. Cl.[7] ................................................. A61B 17/10
[52] U.S. Cl. ......................... 606/140; 606/139; 604/272
[58] Field of Search .................................. 606/139–148, 606/119, 135, 110, 113, 114, 127, 151, 157; 604/272

[56] References Cited

U.S. PATENT DOCUMENTS

| | | |
|---|---|---|
| 2,737,181 | 3/1956 | Beard . |
| 3,155,094 | 11/1964 | Hamilton . |
| 3,382,273 | 5/1968 | Banich et al. . |
| 3,687,138 | 8/1972 | Jarvik . |
| 3,760,810 | 9/1973 | Van Hoorn . |
| 3,834,392 | 9/1974 | Lampman et al. . |
| 3,870,048 | 3/1975 | Yoon . |
| 3,911,923 | 10/1975 | Yoon . |
| 3,934,589 | 1/1976 | Zimmer . |
| 3,958,576 | 5/1976 | Komiya . |
| 3,967,625 | 7/1976 | Yoon . |
| 3,989,049 | 11/1976 | Yoon . |
| 4,085,743 | 4/1978 | Yoon . |
| 4,103,680 | 8/1978 | Yoon . |
| 4,222,380 | 9/1980 | Terayama . |
| 4,226,239 | 10/1980 | Polk et al. . |
| 4,230,116 | 10/1980 | Watson . |
| 4,257,419 | 3/1981 | Goltner et al. . |
| 4,257,420 | 3/1981 | Terayama . |
| 4,267,839 | 5/1981 | Laufe et al. . |
| 4,374,523 | 2/1983 | Yoon . |
| 4,471,766 | 9/1984 | Terayama . |
| 4,548,201 | 10/1985 | Yoon . |
| 4,735,194 | 4/1988 | Stiegmann . |
| 4,794,927 | 1/1989 | Yoon . |
| 4,990,152 | 2/1991 | Yoon . |
| 5,026,379 | 6/1991 | Yoon . |
| 5,122,149 | 6/1992 | Broome . |
| 5,203,863 | 4/1993 | Bidoia . |
| 5,236,434 | 8/1993 | Callicrate . |
| 5,320,630 | 6/1994 | Ahmed ..................................... 606/140 |
| 5,423,834 | 6/1995 | Ahmed ..................................... 606/140 |
| 5,425,736 | 6/1995 | Wadsworth . |
| 5,462,559 | 10/1995 | Ahmed . |
| 5,507,797 | 4/1996 | Suzuki et al. . |
| 5,569,268 | 10/1996 | Hosoda . |
| 5,697,940 | 12/1997 | Chu et al. ............................... 606/140 |

*Primary Examiner*—Glenn K. Dawson
*Attorney, Agent, or Firm*—Kenyon & Kenyon

[57] ABSTRACT

A ligating band dispenser for dispensing a plurality of ligating bands individually during a sequence of operations for a ligating instrument. Interfitted housing and piston segments support a plurality of ligating bands at axially spaced locations. Retraction of the piston segment dispenses one ligating band and shifts the remaining ligating bands distally and axially. After retraction, the piston is biased forward so a next retraction dispenses another ligating band. A sclerotherapy needle mounts in a sheath that connects to the piston segment. A physician retracts the sheath to retract the piston. In addition the physician can advance the sclerotherapy needle through the sheath to administer a sclerotherapy agent as an alternative to ligating a lesion.

20 Claims, 7 Drawing Sheets

COMBINED MULTIPLE LIGATING BAND DISPENSER AND SCLEROTHERAPY NEEDLE INSTRUMENT

CROSS REFERENCE TO RELATED APPLICATION

This application is a continuation of application Ser. No. 08/324,132, filed on Oct. 14, 1994, now U.S. Pat. No. 5,697,940, and CIP of Ser. No. 07/960,081, filed Oct. 9, 1992, now U.S. Pat. No. 5,269,789.

BACKGROUND OF THE INVENTION

1. Field of the Invention

This invention generally relates to ligating instruments and more particularly to instruments capable of dispensing ligating bands in a sequential manner.

2. Description of Related Art

The treatment of various types of lesions including internal hemorrhoids by ligation is well known. The object of ligation is to position an elastic cord, or ligating band, at the lesion to stop circulation through tissue and allow the tissue to die whereupon the body sloughs off the dead tissue. When lesions are located deep in the alimentary tract, physicians generally use either band ligation or sclerotherapy. However, they prefer to make that selection after viewing the lesion endoscopically. With prior art devices, a physician must then select either band ligation or sclerotherapy apparatus for insertion through a working channel of the endoscope.

The following patents disclose various embodiments of ligating band dispensing instruments and apparatus useful for sclerotherapy:

3,760,810 (1973) Van Hoorn
4,222,380 (1980) Terayama
4,257,419 (1981) Göltner et al
4,735,194 (1988) Stiegmann U.S. Pat. No. 3,760,810 to Van Hoorn discloses an instrument for facilitating the placement of a single ligating band or set of bands. The instrument includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The inner tube can be loaded with a set of one or more elastic rings or ligating bands. A separate stopper bar attaches to the instrument to prevent premature dispensing. When the instrument is located proximate a lesion, a physician removes the stopper bar and applies vacuum to draw tissue into a hollow passage at the distal end of the instrument. Pulling on the trigger retracts the inner tube. A radial surface or shoulder on the outer tube engages the ligating band so it can not displace with the inner tube. As the inner tube is withdrawn from the ligating band, it collapses onto the tissue.

U.S. Pat. No. 4,222,380 to Terayama discloses apparatus adapted for sclerotherapy in the form of a celiac injector for injecting a medical fluid into desired celiac tissue. In the specifically disclosed apparatus a medical fluid supply tube with an injector needle fixed at its tip end thereof and an elongated member fitted at its tip end with a plurality of claw wire elements are relatively slidably housed in an outer sheath. By manual operations of the respective proximal end portions of the supply tube and elongated member, the claw wire elements take hold of a tissue portion at a desired part, the needle is stabbed into the held tissue portion, and the medical fluid supplied through the supply tube is injected into the tissue by means of the injector needle.

U.S. Pat. No. 4,257,419 to Göltner et al discloses a rigid endoscope that includes a ligating band dispenser with an inner tube that moves with respect to an outer tube to dispense a ligating band. This dispenser is oriented at right angles to the rigid endoscope and includes a structure for moving the inner tube of the dispenser in this configuration.

U.S. Pat. No. 4,735,194 to Stiegmann discloses a flexible endoscope ligating instrument in which a flexible endoscope structure includes a biopsy channel and a suction channel extending between the proximal and distal ends. A dispenser, like the dispenser structure shown in the Van Hoorn and Göltner patents, includes an inner tube that moves axially with respect to an outer tube at the distal end of the instrument. The outer tube connects to the distal end of the endoscope. An operating mechanism in the form of a pull wire with a weighted handle maintains tension on the inner tube so it does not displace axially outward while the instrument is being positioned. For some applications it is suggested that the endoscope structure be inserted through an overtube to prevent premature dispensing. Suction can be applied to draw tissue into a central aperture of the dispenser. Then a physician pulls the handle and retracts the inner tube axially past the distal end of the outer tube to force the ligating band off the instrument onto the tissue.

Each of the instruments disclosed in the Van Hoorn, Göltner and Stiegmann patents dispenses a single ligating band or a single set of ligating bands at a single location. None of the patents suggests dispensing ligating bands at discrete locations. The Van Hoorn patent does disclose the possibility of depositing plural ligating bands. However, Van Hoorn seems only to suggest dispensing plural ligating bands at a single site in a single operation. The apparatus disclosed in the Van Hoorn, Göltner or Stiegmann patents apparently would have to rely on a physician's sense of touch in order to displace the inner tube by an incremental distance corresponding to the thickness of a stretched ligating band to deposit a plurality of bands at different sites. That would be very difficult to accomplish.

Indeed, when it is desired to deposit ligating bands at different sites, the common practice is to withdraw the entire instrument from the patient and load a new ligating band onto the inner tube. Loading ligating bands on an instrument requires special tools and can be time consuming particularly if the special tooling must be retrieved to install each ligating band individually while the instrument is withdrawn. Each of these instruments requires some structure, such as special stoppers or overtubes, for preventing the premature dispensing of the ligating band. Consequently, none of these instruments is readily adapted for dispensing ligating bands at different sites without withdrawing the instrument after each individual site is ligated.

Each of the instruments in the Van Hoorn, Göltner and Stiegmann patents also is dedicated to band ligation therapy. There is no suggestion that this apparatus can or should be combined with any other apparatus for performing any other procedure such as sclerotherapy. Similarly the Terayama patent discloses apparatus that is dedicated to celiac injection. There is no suggestion that this apparatus can or should be combined with any other apparatus for performing any other procedure, such as band ligation.

In current practice a physician normally begins therapy by visualizing some or all of the lesions with an endoscope to establish a therapy plan. Then the physician withdraws the endoscope to add either a ligating band dispenser or sclerotherapy apparatus. Next, the physician reinserts the endoscope to perform the desired therapy. If the physician decides on a different therapy for a subsequent lesion or the use of both sclerotherapy and ligating band therapy on a single lesion, the physician withdraws the endoscope, changes the apparatus and reintroduces the modified endoscope. This withdrawal and replacement procedure will be required if successive lesions are to be treated alternately by band ligation or if successive lesions are to be treated by band ligation and sclerotherapy. It is only when successive lesions are to be treated by sclerotherapy that the withdrawal replacement procedure is avoided. As will be apparent, these procedures complicate the physician's work and prolong the time required to treat the lesions.

SUMMARY

Thus it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

Still another object of this invention is to provide a dispenser for attachment to a ligating instrument that dispenses plural ligating bands at different locations, that is reliable and easy to use and that inherently prevents any premature dispensing of the ligating band during instrument positioning.

Yet still another object of this invention is to provide an improved method for applying multiple ligating bands at discrete sites without having to withdraw a ligating instrument after each ligation.

Another object of this invention is to provide an instrument adapted for band ligation and sclerotherapy of successive lesions without requiring withdrawal of the instrument.

Yet another object of this invention is to provide an instrument adapted for band ligation and sclerotherapy that can deposit individual ligating bands at different sites without requiring withdrawal of the instrument.

Still another object of this invention is to provide an instrument adapted for band ligation and sclerotherapy that is easy to use and prevents any premature dispensing of a ligating band during instrument positioning and use.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
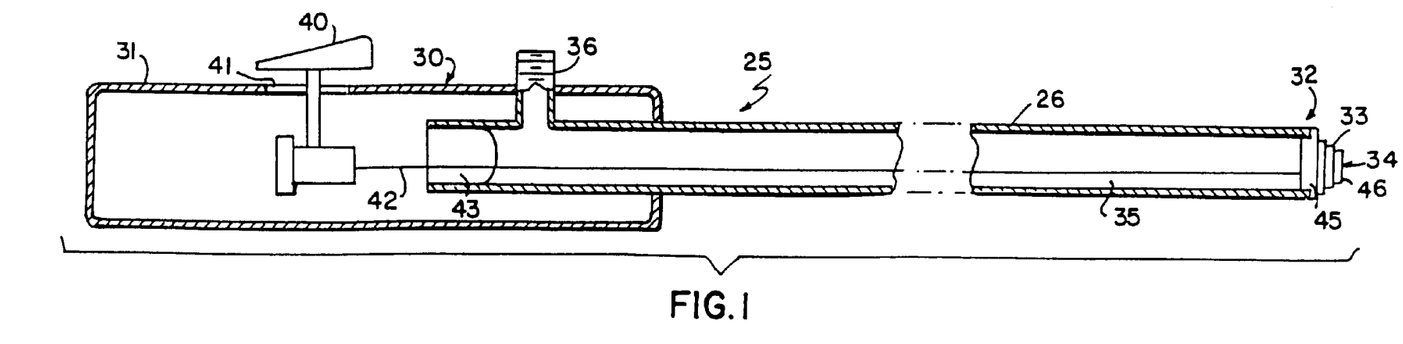
FIG. 1 depicts one embodiment of a ligating instrument constructed in accordance with this invention.

FIG. 1 depicts, in schematic form, one embodiment of a ligating instrument 25 that dispenses elastic ligating bands during a succession of operations. The ligating instrument includes an introducer in the form of an elongated, rigid tubular housing 26. A proximal end 30 of the tubular housing 26 connects to a handle 31 while the distal end 32 connects to a dispenser 33. The dispenser 33 is formed in a hollow tubular form to provide a central passage 34 that communicates with a central passage 35 through the tubular housing 26. A vacuum port 36 exits the tubular housing 26 at a proximal end 30 thereof through an aperture in the handle 31.

The handle 31 carries a trigger 40 that can be displaced axially in a slot 41. The trigger 40 attaches to a pull wire 42 that passes through a proximal seal 43 located at the proximal end 30 of the tubular housing 26 and connects to the dispenser 33. Diverse implementations of such a trigger and pull-wire operating structure can be incorporated in ligating instruments. The specifically disclosed embodiment is merely representative of such diverse implementations.

The proximal seal 43 allows vacuum to be applied through the vacuum port 36 and the central passages 34 and 35 while allowing reciprocal motion of the pull wire 42. With the proximal seal 43 in place, vacuum applied to the vacuum port 36 draws tissue into the central passage 34 for ligation. The trigger 40 and pull wire 42 constitute an operating structure that enables a physician to operate the dispenser 33, at the distal end 32, of the instrument 25 from the proximal end 30.

Figure 2:
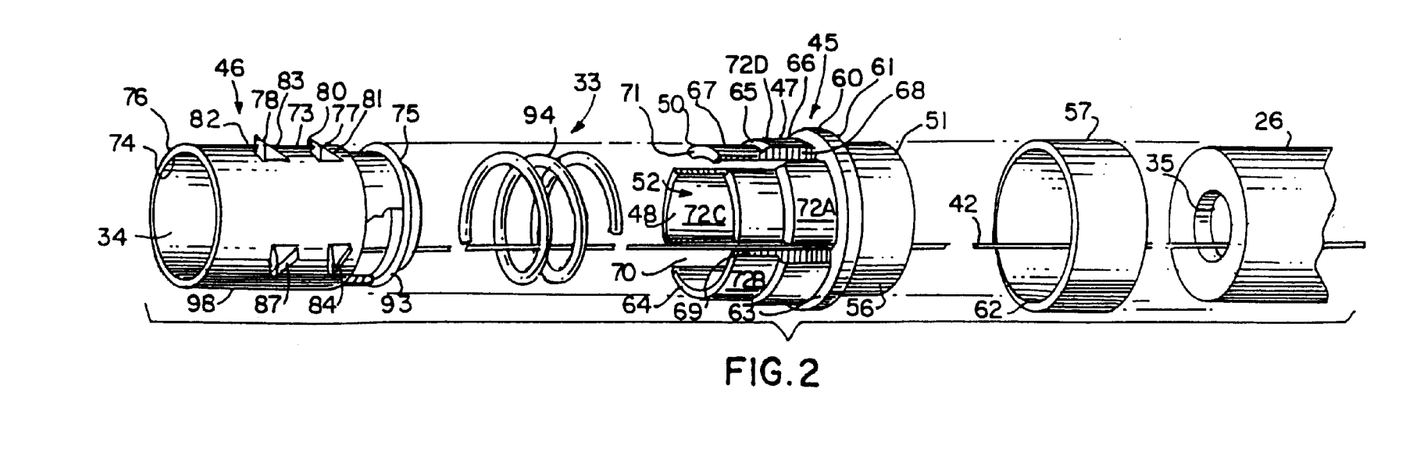
FIG. 2 is a perspective view of one embodiment of a ligating instrument dispenser constructed in accordance with this invention.

Referring to FIGS. 1 and 2, the dispenser 33 includes a housing segment 45 that attaches to the tubular housing 26. A piston segment 46 reciprocates with respect to the housing segment 45 between first and second positions under the control of the pull wire 42 or other structure.

Figure 3:
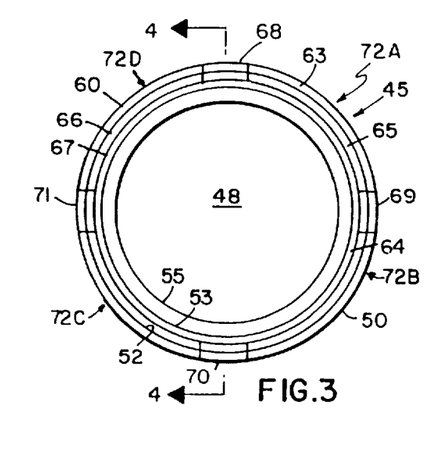
FIGS. 3 and 4 are views of a housing segment for use in the dispenser of FIG. 2 with FIG. 4 being a section taken along lines 4—4 in FIG. 3.
Figure 4:
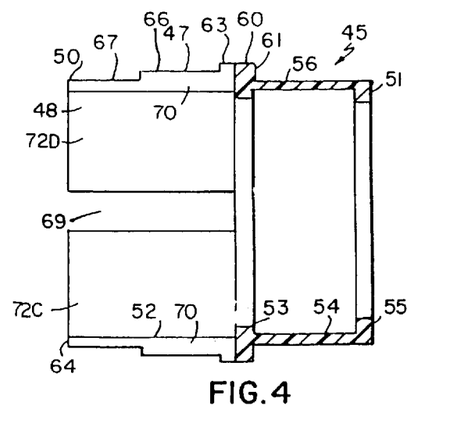

As shown in FIGS. 2 through 4, the housing segment 45 is formed as a generally tubular structure 47 with a central passage 48 between a distal housing end 50 and a proximal housing end 51. The tubular structure 47 has a first inner cylindrical surface 52 extending from the distal end 50 to an intermediately located circumferential central bead 53. A second inner cylindrical surface 54 shown in FIG. 4 extends from the central bead 53 to an annular, inturned, radially extending lip 55 at the proximal end 51.

Figure 7:
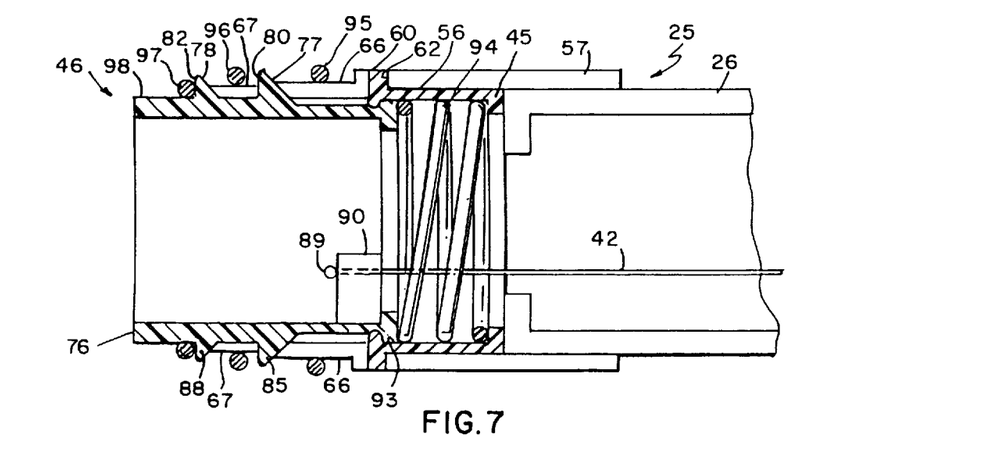
FIGS. 7 through 9 depict the assembly of the housing and piston segments of FIGS. 3 through 6 at different orientations.

In this particular embodiment an outer cylindrical surface 56, that is coextensive with the inner cylindrical surface 54 and the annular lip 55, provides an axially extending, cylindrical base means for connecting the housing segment 45 to the tubular housing 26 of FIGS. 1 and 2. As shown in FIG. 7, elastic, tubing 57 overlies the outer cylindrical surface 56 and the distal end of the tubular housing 26 to affix the housing segment 45 to the tubular housing 26. A band 60 in FIGS. 3, 4 and 7 aligns axially with the central bead 53 to provide a shoulder 61 that receives an end 62 of the tube 57. The overlying tubing 57 can be replaced by any number of connecting structures that include threaded and mechanically or chemically bonded structures. The objective of any such structure is merely to affix the housing segment 45 to the end of the housing 26.

The portion of the housing segment 45 extending distally from the band 60 provides three axially spaced, radially extending shoulders including a shoulder 63 at the band 60, a shoulder 64 at the distal end 50 and an intermediate shoulder 65. These shoulders define limits of intermediate cylindrical surfaces 66 and 67. The cylindrical surface 67 is formed with a diameter that is less than the diameter of the cylindrical surface 66. As described particularly later, the resulting stepped cylindrical surfaces 66 and 67 are adapted for supporting ligating bands at axially spaced positions on the housing segment 45.

Still referring to FIGS. 2 through 4, each of the surfaces 66 and 67 has a generally cylindrical form divided into one of several arcuate fingers by axially extending slots 68, 69, 70 and 71. Finger 72A lies between slots 68 and 69; finger 72B, between slots 69 and 70; finger 72C, between slots 70 and 71; and finger 72D between slot 71 and 68.

Figure 5:
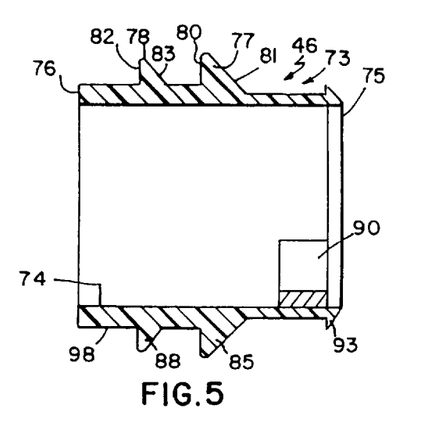
FIGS. 5 and 6 are views of a piston segment useful in the dispenser of FIG. 2 with FIG. 5 being a section taken along 5—5 in FIG. 6.
Figure 6:
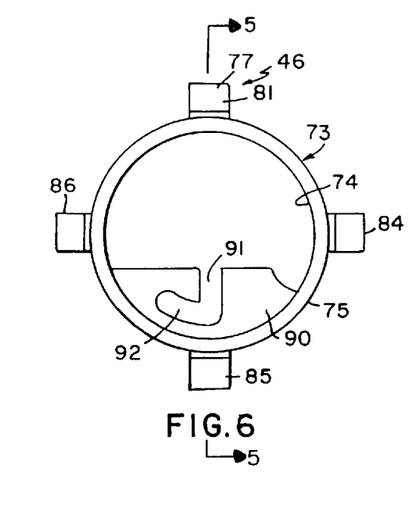

Now referring to FIGS. 2, 5 and 6, the piston segment 46 comprises a cylindrical base or tube 73 with an essentially inner cylindrical surface 74 between a proximal end 75 and a distal end 76. The tube 73 is formed with a plurality of circumferentially and-axially spaced, radially extending fingers. Fingers 77 and 78, for example, are spaced axially with respect to each other and align with the slot 68. Each finger has a triangular cross section. For example, the finger 77 defines a distally facing, radial shoulder 80 and a proximally facing ramp surface 81. Likewise the finger 78 includes a distally facing shoulder 82 and a proximally facing ramp surface 83. The height of the finger 77 is greater that the height of the finger 78. As shown more particularly in FIG. 7, this height difference corresponds to the steps in the housing segment 45, so the shoulder 80 extends radially beyond the surface 66 of the housing segment 45 while the shoulder 82 extends radially beyond the surface 67.

The piston segment 46 additionally includes circumferentially spaced fingers 84, 85 and 86 aligned axially with the finger 77 and having the same relative form as the finger 77. Another set of circumferentially spaced fingers aligns axially with and have the same form as the finger 78. One such finger 87 is shown in FIG. 2; a finger 88 is shown in FIG. 5; another finger, not shown, aligns with the finger 86.

As shown in FIGS. 2 and 7, the pull wire 42 connects to the piston segment 46. In this specific embodiment the pull wire 42 terminates with a bead-like, enlarged head structure 89. As shown in FIGS. 5 and 6, the piston segment 46 includes a transverse member 90 adjacent the proximal end 75. A radially extending slot 91 leads from the interior of the tube 73 to an arcuate slot 92 located adjacent the tube 73. In practice the pull wire 42 passes through the slot 91 into the slot 92. Thereafter tension on the pull wire 42 causes the head 89 to engage a surface of the transverse member 90 adjacent the slot 92. The angle between the slots 91 and 92 minimizes any tendency of the pull wire 42 to disengage from the transverse member 90 while tension is applied.

As shown in FIGS. 2, 6 and 7, the proximal end 75 of the piston segment 46 terminates with frusto-conical lip 93 that tapers toward the proximal end 75. The lip 93 is configured to snap over the central bead 53 of the housing segment 45 thereby to limit distal motion of the piston segment 46 relative to the housing segment 45.

Referring again to FIGS. 2 and 7, the dispenser 33 is assembled by inserting a compression spring 94 into the housing segment 45 from the distal end 50 to be located intermediate the central bead 53 and the annular lip 55. In this position, the spring 94 is partially compressed. The piston segment 46 is inserted into the housing segment 45 until the lip 93 snaps over the central bead 53. Next the dispenser 33 can be mounted to a housing 26 as shown in FIG. 7 by a tube 57 or similar means. In this embodiment the pull wire 42 extends from the piston segment 46 through the spring 94 and the housing 26 to the proximal end thereof.

Prior to using the instrument 25, a plurality of elastic ligating bands are mounted on the dispenser 33 generally by using tooling that is similar to the tooling used with prior art ligating instruments. A first ligating band 95 is stretched onto the cylindrical surface 66; and a second ligating band 96, onto the surface 67. A third ligating band is stretched onto a distal end surface 98 of the piston segment 46.

In use the physician initially positions the distal end 76 of the piston segment 46 closely adjacent to the tissue to be ligated. If the ligating instrument 25 has a vacuum port, suction is used to draw the tissue into the instrument through the distal end 76.

Figure 8:
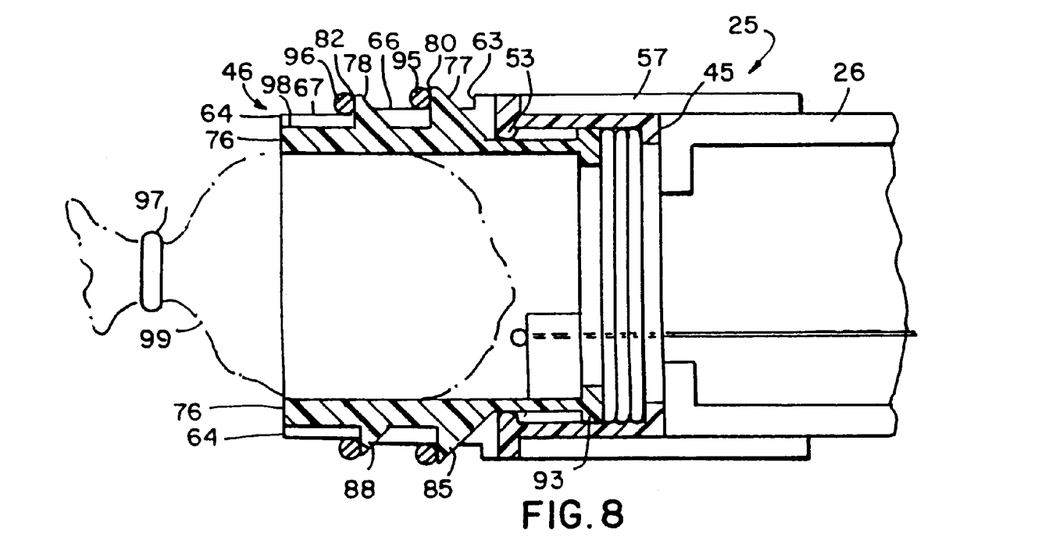

When the physician thereafter retracts the trigger 40 in FIG. 1, the pull wire 42 moves the piston segment 46 proximally with respect to the housing segment 45 from the position shown in FIG. 7 to the position shown in FIG. 8. This further compresses the spring 94. When the fingers, such as fingers 77 and 85, abut the shoulder 63, or some other stop engages, retraction terminates. During this retraction to a well defined end position, the shoulder 64 formed by the housing segment 45 at the distal end 50 thereof slides over the surface 98 of the piston segment 46 and engages the ligating band 97. Continued retraction of the piston segment 46 causes the ligating band 97 to move over the surface 98 until it reaches the distal end 76 and collapses from the surface 98 to ligate the tissue 99.

Simultaneously each of the fingers, such as fingers 77 and 78, 85 and 88, also retract. Initially the ramp surfaces of each finger will engage each correspondingly positioned ligating band. For example, during the operation depicted in FIGS. 7 and 8, the ramp surfaces of the fingers 77 and 85 initially engage the ligating band 95 while the fingers including fingers 78 and 88 engage the ligating band 96. As these fingers essentially make point contact with the ligating bands, the bands 95 and 96 expand locally and radially. However, the shoulders 63 and 65 prevent any proximal axial displacement of the bands 95 and 96. As the fingers pass the ligating bands, as shown particularly in FIG. 8, the bands drop to positions that are distally located with respect to the fingers. For example, the ligating band 96 lies against the shoulder 82 of the finger 78 while the ligating band 95 lies against the shoulder 80 of the finger 77. Consequently only one ligating band 97 is dispensed when the instrument 25 is positioned as shown in FIG. 8. The remaining ligating bands 95 and 96 remain on the instrument 25.

Figure 9:
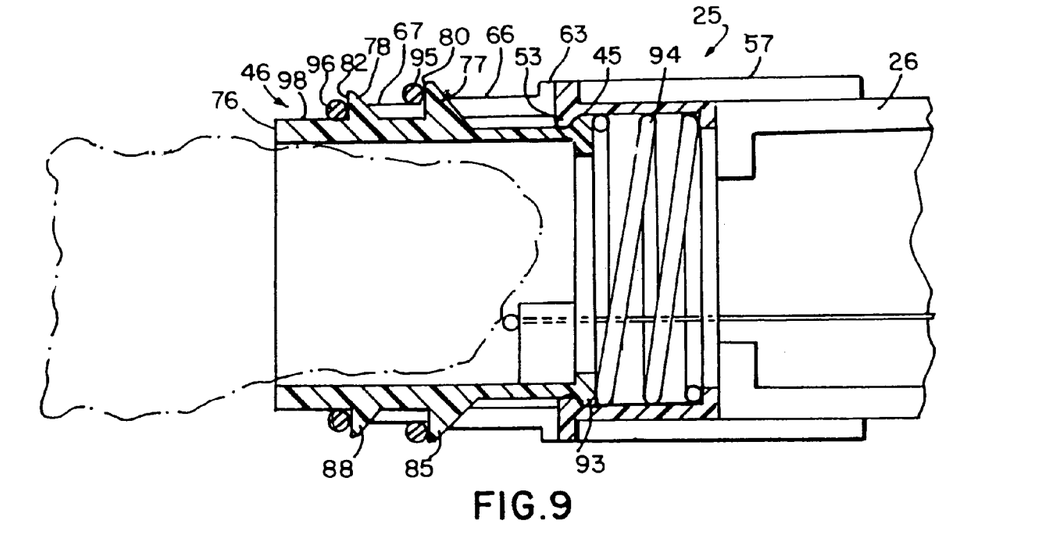

When the physician releases the trigger 40 in FIG. 1, the spring 94 drives the piston segment 46 distally until the lip 93 engages the central bead 53 as shown in FIGS. 8 and 9. During this motion, the various fingers, including fingers 77, 78, 85 and 88 advance the ligating bands 95 and 96 distally and axially. More specifically the circumferentially aligned fingers, including fingers 78 and 88, drive the ligating band 96 distally from the surface 67 onto the surface 98. The other aligned fingers, including fingers 77 and 85 drive the ligating band 95 from the surface 66 to the distal end surface 67 of the housing segment 46.

Now the physician can immediately position the distal end 76 of the instrument proximate another area for ligation and repeat the sequence. Consequently in this particular embodiment, it is possible for the physician to ligate three areas without removing the ligating instrument 25 from the patient. Each ligation merely requires the physician to position the instrument, to draw tissue into the instrument, to pull a trigger between two limited positions to dispense a single ligating band and release the trigger to prepare for a second sequence. There is no necessity for the physician to remove the instrument or to exercise sensitive and difficult control over the relative position of the piston segment 46 in order to provide this sequential dispensing operation.

These and other advantages are achieved by the coaxial configuration of the housing segment 45 and piston segment 46 as interfitted segments for supporting the ligating bands at the plurality of axially spaced positions, as on surfaces 66, 67 and 98. The fingers, such as fingers 77 and 78, engage the ligating bands, so the piston segment 46 can move between a first position as shown in FIG. 7 and a second position as shown in FIG. 8 and dispense one ligating band from the distal end of the ligating instrument 25. The subsequent return of the piston segment 46 with its fingers moves each of the remaining ligating bands distally and axially with respect to the ligating instrument 25 to prepare for a next operation. Moreover, the spring 94 biases the piston segment 46 distally with sufficient force to prevent premature dispensing of a ligating band from the surface 98.

Figure 10:
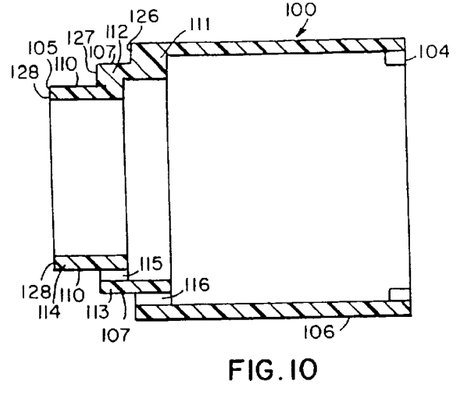
FIG. 10 is a view of a housing segment of another dispenser constructed in accordance with this invention.
Figure 11:
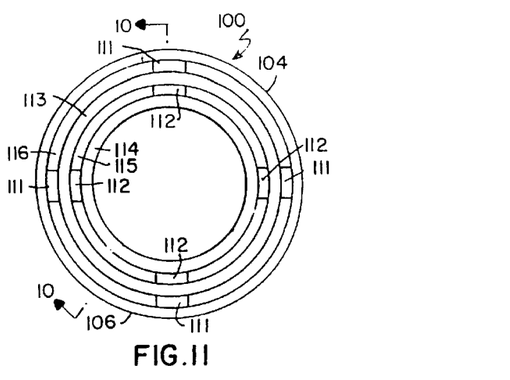
FIG. 11 is an end view taken from the left side of FIG. 10.
Figure 12:
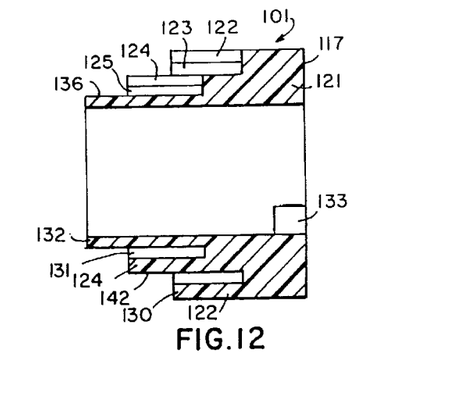
FIG. 12 is a view of a piston useful with the housing shown in FIGS. 10 and 11.
Figure 13:
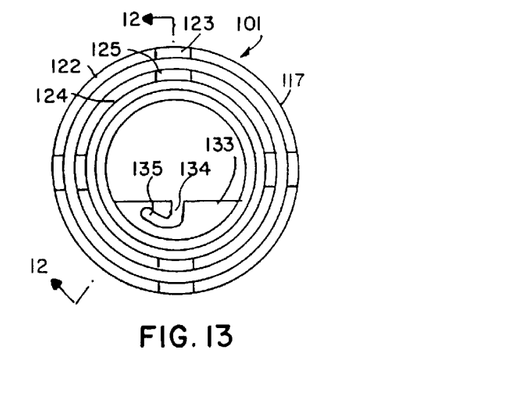
FIG. 13 is an end view taken from the left side of FIG. 12.
Figure 14:
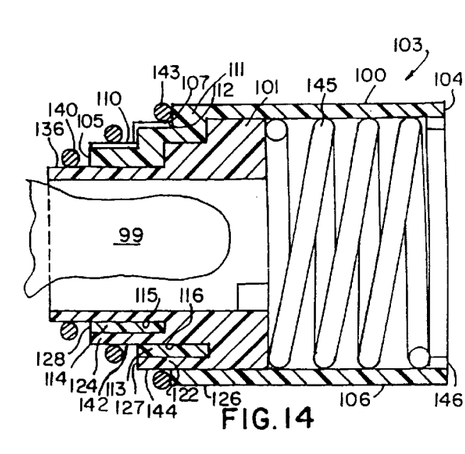
FIGS. 14 and 15 are views of an assembly of the housing and piston embodiment shown in FIGS. 10 through 13 at different orientations.
Figure 15:
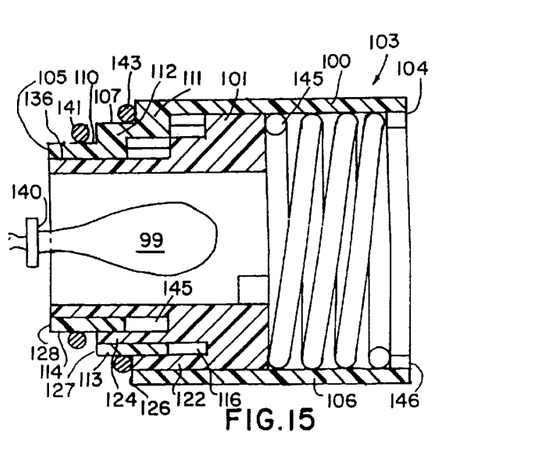

FIGS. 10 through 15 depict another embodiment of a dispenser for providing a similar operation. This dispenser is also adapted for use with a ligating instrument 25 such as shown in FIG. 1 or other introducers that may include a rigid or flexible endoscopic device. In this particular embodiment, a housing segment 100, as shown in FIGS. 10 and 11, and a piston segment 101, as shown in FIGS. 12 and 13, form a dispenser 103 as shown in FIGS. 14 and 15.

Referring to FIGS. 10 and 11, the housing segment 100 extends between a proximal end 104 and a distal end 105 and has a main cylindrical body portion 106. As the housing segment 100 extends toward the distal end 105, it forms a series of stepped surfaces of decreasing radius that include an intermediate surface 107 and a distally located surface 110.

The housing segment 100 is integrally molded with a plurality of connecting portions 111 and 112 equiangularly spaced about the housing segment 100. In the specific embodiment shown in FIGS. 10 and 11, the connecting portions 111 and 112 are spaced by 90°; however, other angles can also be used. The connecting portions 111 and 112 support the remaining portions of the housing segment 100 that form annular, ring-like structures 113 and 114 intermediate the connecting portions 111 and 112. The annular structures 113 and 114 are radially displaced with respect to other portions of the housing segment 100 to define a plurality of arcuate openings 115 and 116 intermediate each of the structures 112 and 111 respectively. The openings 115 and 116 receive interfitting portions of the piston segment 101.

FIGS. 12 and 13 disclose the piston segment 101 that extends between a proximal end 117 and a distal end 120 and has a solid ring structure 121 at the proximal end that constitutes a cylindrical body portion. A series of arcuate segments extend at different radii from this ring 121. For example, outer arcuate segments 122 are disposed at a maximum radius. These segments 122 are interrupted by axially extending slots 123. The diameter of the openings 116 determines the diameter of the arcuate segments 122 in the housing segment 100 shown in FIG. 10. Another set of arcuate segments 124 are formed at smaller radius and are interrupted by slots 125. The diameter of the arcuate openings 115 determine the diameter of the arcuate segments 124.

Referring again to FIGS. 10 and 11, the connecting portion 111 defines a first shoulder 126. The structures 113 terminate with second shoulders 127 that are axially and distally displaced with respect to the shoulder 126. The structures 114 terminate in shoulders 128 at the distal end 105. Thus, the shoulders 126, 127 and 128 and the surfaces 107 and 110 form an axially displaced, distally extending stepped surface. Similarly, the segments 122 in the piston segment 101, as shown in FIG. 12, form a shoulder 130. The distal end of the segment 124 forms a shoulder 131 and at the distal end there is a shoulder 132.

The piston segment 101 additionally includes a transverse structure 133 that includes a radial slot 134 and an arcuate slot 135 for capturing a distal end of a pull wire. This structure 133 is analogous to the transverse structure 90 and slots 91 and 92 shown in FIG. 6.

During assembly, the piston segment 101 of FIGS. 12 and 13 mounts, in an interfitting fashion, in the housing segment 100 shown in FIGS. 10 and 11 from the proximal end 104. As shown in FIGS. 14 and 15, each of the arcuate segments 122 and 124 interfit with the arcuate apertures 116 and 115. In a fully extended position as shown in FIG. 14, a distal end surface 136 on the piston segment 101 extends beyond the distal end 105 of the housing segment 100. This surface 136 receives a ligating band 140. A second ligating band 141 lies on a surface 142 intermediate the shoulders 130 and 131. A third ligating band 143 lies on a surface 144 that extends proximally from the shoulder 130.

When a ligating instrument, attached to the dispenser 103 shown in FIGS. 14 and 15 is properly positioned, suction can be applied to draw the tissue 99 into the dispenser 103 along its axis. Then the physician retracts the piston segment 101 proximally with respect to the housing segment 100. That motion compresses a spring 145. The shoulders 126, 127 and 128 engage the ligating bands 143, 141 and 140, respectively to hold them in a fixed position relative to the housing segment 100 during this motion. When the piston segment 101 reaches its fully retracted position, as shown in FIG. 15, the ligating band 140 is pushed off the surface 136 to ligate the tissue 99. The shoulder 127 transfers the second ligating band 141 from the surface 142 to the surface 136. Likewise the shoulder 126 transfers the ligating band 143 from the surface 144 to the surface 142.

When the physician releases the trigger, the spring 145 advances the piston segment 101 distally back to the position shown in FIG. 14 except that the ligating bands 141 and 143 now lie where the ligating bands 140 and 141 were previously. The ligating instrument is then ready to dispense the ligating band 141 at some other site.

FIGS. 14 and 15 disclose a collar 146 that could be ultrasonically welded to the proximal end 104 of housing segment 100 after assembly. This collar 146 would capture the spring 145 and the piston segment 101 in the housing segment 100. Other structures could be substituted. For example the distal end of an introducer, such as tubular housing 26 in FIG. 1, could abut the proximal end 104 of the housing segment 100 to confine the spring 145, other structures could accommodate other alternatives for the introducer such as those including endoscopic structures.

Figure 16:
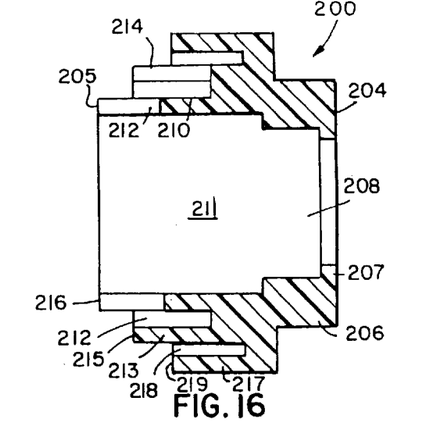
FIG. 16 is a view of a housing segment for another dispenser constructed in accordance with this invention.
Figure 17:
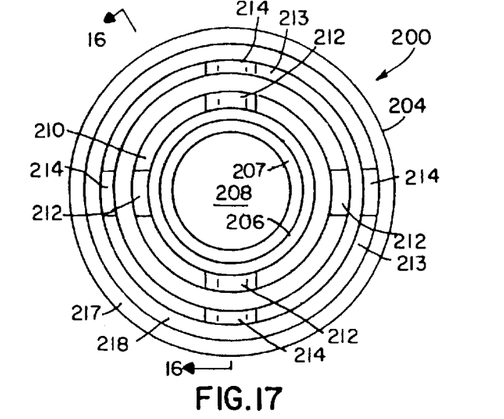
FIG. 17 is an end view taken from the left side of FIG. 16.
Figure 18:
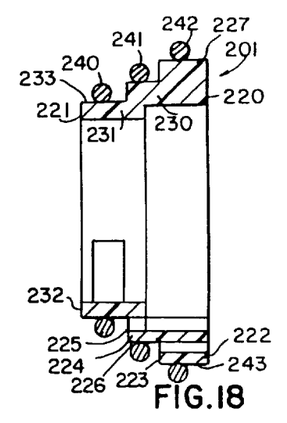
FIG. 18 is a view of a piston useful with the housing shown in FIGS. 16 and 17.
Figure 19:
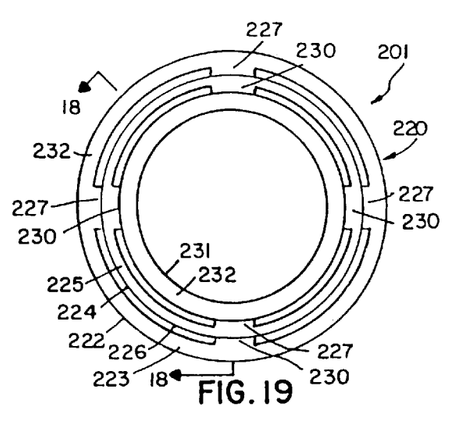
FIG. 19 is an end view taken from the left side of FIG. 18.
Figure 20:
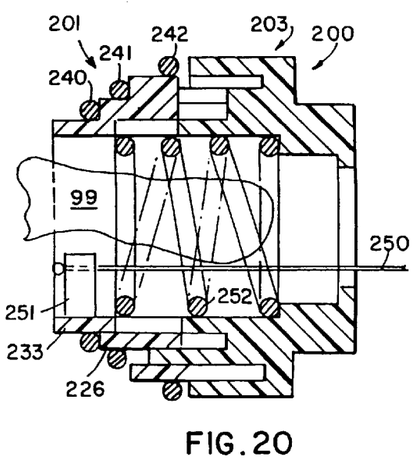
FIGS. 20 and 21 are views of an assembly of the housing and piston embodiments shown in FIGS. 16 through 19 at different orientations.
Figure 21:
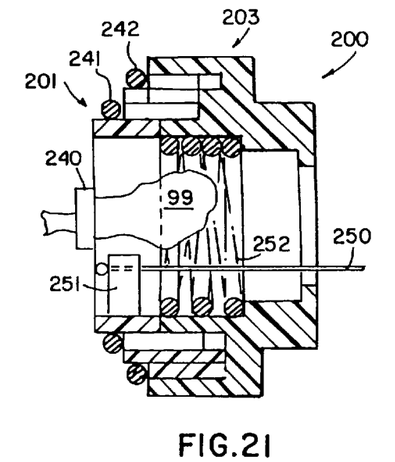

FIGS. 16 through 21 disclose another embodiment of a dispenser that includes a housing 200 shown in FIGS. 16 and 17 and a piston segment 201 shown in FIGS. 18 and 19 that are assembled into a dispenser 203 shown in FIGS. 20 and 21. The housing 200 extends from a proximal end 204 to a distal end 205. A ring-like body structure 206 at the distal end 205 has an inturned lip 207 and defines an internal chamber 208 of a given radius. A first series of axially extending fingers 210 extend from the structure 206 and form a second chamber 211 that has a larger radius than the chamber 208.

Equiangularly spaced axially extending slots 212, spaced at 90° in this particular embodiment, define four fingers 210 that axially extend from the ring 206 to the distal end 205. The ring 206 also supports another set of axially extending fingers 213 separated by equiangularly spaced slots 214. The fingers 213 terminate with distal end shoulders 215 that are proximally and axially spaced from shoulders 216 formed by the arcuate fingers 210. The fingers 213 lie on a radius that is greater than the radius that the fingers 210 define. The ring 206 also supports an arcuate ring 217 that is radially outwardly spaced from the fingers 213 and forms a channel 218. The ring 217 terminates with a shoulder 219.

The piston segment 201 shown in FIGS. 18 and 19 extends between a proximal end 220 and a distal end 221. A ring structure 222 at the proximal end has a diameter that corresponds to the nominal diameter of the channel 218 between the fingers 213 and 217 of the housing segment 200 in FIGS. 16 and 17. The ring structure 222 in FIGS. 18 and 19 terminates in a distal shoulder 223. A second ring structure 224, radially inwardly spaced from the ring structure 222, terminates distally in a shoulder 225. The shoulder 225 is axially offset in a distal direction respect to the shoulder 223 thereby to define an exterior cylindrical surface 226 intermediate the shoulder 223 and 225. Equiangularly spaced extensions 227 align with the slots 214 in FIGS. 16 and 17 and interconnect the ring structures 222 and 224. Other equiangularly spaced extensions 230 align with slots 212 and interconnect the ring structure 224 with an inwardly radially spaced ring 231 structure. The ring structure 231 terminates at the distal end 221 with a shoulder 232 and that forms another exterior cylindrical surface 233 between the shoulders 225 and 232.

The piston segment 201 shown in FIGS. 18 and 19 can be used as a replaceable structure that is preloaded with ligating bands, such as ligating bands 240, 241 and 242. As shown in FIG. 18, the surfaces 233, 226 and a surface 243 support these ligating bands.

The piston segment 201 can be attached to the distal end 205 of the housing segment 200 shown in FIGS. 20 and 21. A pull wire 250, analogous to the pull wire 42 in FIG. 1, connects to a transverse attachment structure 251 formed inside the piston segment 201. A modification to the trigger could allow the extension of the trigger and the pull wire 250 by means of appropriate interlocking structure to a loading position to accommodate a replaceable piston segment 201. Such a structure would enable the pull wire 250 to extend for a distance sufficient to allow its ready connection to a transverse structure 251. After attachment, the trigger and pull wire 250 would return to a normal extended position as shown in FIG. 20. In this position a compressible spring 252, captured in the chamber 208 and extending distally to engage the transverse structure 251, would bias the piston segment 201 distally with respect to the housing segment 200.

After loading a piston segment 201 and positioning the instrument as shown in FIG. 20, the proximal end 220 of the piston segment 201 would align axially with the end of the ring 217. The combined forces produced by the spring 252 and the pull wire 250 would hold the piston segment 201 in the position shown in FIG. 20. However, the connecting structures 228 and 230 of the piston segment 201 also would align with the slots 214 and 212 of the housing segment 200 thereby to allow the piston segment 201 to move proximally under control of the pull wire 250.

A physician would position the ligating instrument containing the dispenser 203 at tissue 99 as shown in FIG. 20 and use vacuum or mechanical means to draw the tissue 99 into the dispenser 203. When the physician pulls the trigger, the pull wire 250 moves the piston segment 201 proximally to the position shown in FIG. 21. The shoulders 216, 215 and 219 due to their axial offsets, engage the ligating bands 240, 241 and 242 through the slots defined in the piston segment and displace the ligating bands axially with respect to the piston segment 201. At the retracted position shown in FIG. 21, each of these shoulders displaces the ligating bands 240 through 242 beyond the shoulders 232, 225 and 223 respectively. Consequently the ligating band 240 is dispensed to ligate the tissue 99. The ligating band 241 moves to the segment 210 while the ligating band 242 moves to the segment 213.

When the physician releases the trigger, the spring 252 drives the piston segment 201 back to the position shown in FIG. 20. During this movement, the ligating band 241 rides on the surface 233 and advances axially and distally relative to the housing segment 200 while the ligating band 242 rides on the surface 236.

Each of the foregoing three embodiments shown in FIGS. 1 through 9, in FIGS. 10 through 15 and in FIGS. 16 through 21 discloses a ligating band dispenser for a ligating instrument. In each the dispenser can dispense a single ligating band at a given location. It will be apparent, however, multiple bands could be located at each axial position in any of the embodiments. In each of these embodiments a physician performs multiple ligating operations at different locations without having to withdraw the ligating instrument after each ligating band is dispensed.

As previously indicated, physicians often prefer to make a selection between band ligation or sclerotherapy upon visualization of a particular lesion. An instrument shown in FIGS. 22 and 23 enables the physician to make the selection upon visualization without any requirement for withdrawing an instrument. As more specifically shown in FIG. 22, this instrument is adapted for use with an endoscope 300 that extends between a proximal end 301 and a distal end 302 that normally will be positioned closely adjacent a lesion. The endoscope includes a working lumen that extends from the distal end 302 to an endoscope port 304 that provides direct access to the working lumen 303 through a lumen extension 303A shown in FIG. 23. Other lumens are included, but not shown.

In this particular embodiment, a ligature dispenser 305 attaches to the distal end 302 of the endoscope 300 and corresponds to the dispenser shown in FIGS. 2 through 9. More specifically the dispenser 305 includes a housing 306 and piston 307 for enabling the sequential operations by which ligature bands 310, 311 and 312 can be deposited over a lesion that is pulled into the housing by suction or other means. The piston 307 is movable between first and second positions relative to the housing 306 that attaches-to the endoscope 300 by means of a connector represented as a connector tubing 313. A spring 314 drives the piston 307 to an extended or distal position relative to the housing 306. A transverse member 315 having a cross-sectional form as shown in FIG. 6, but elongated somewhat axially within the piston 307 establishes a point at which an operator attaches to the piston 307 to enable a physician to withdraw or retract the piston proximally with respect to the endoscope as a first step in dispensing a ligating band such as the ligating band 310 shown in FIG. 22.

Figure 22:
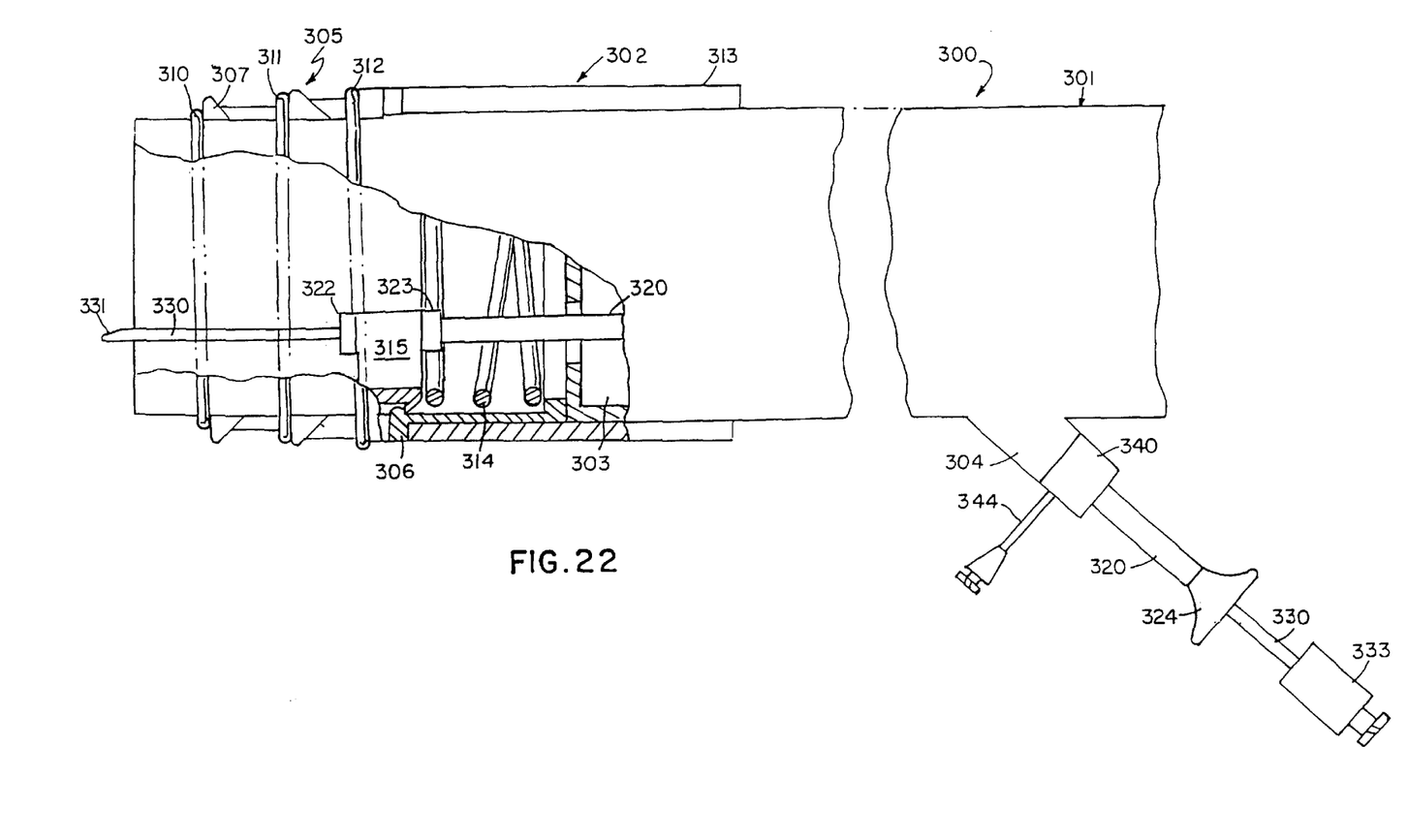
FIG. 22 is a view, partially in section, of a combined ligating band dispenser and sclerotherapy needle instrument constructed in accordance with this invention.
Figure 23:
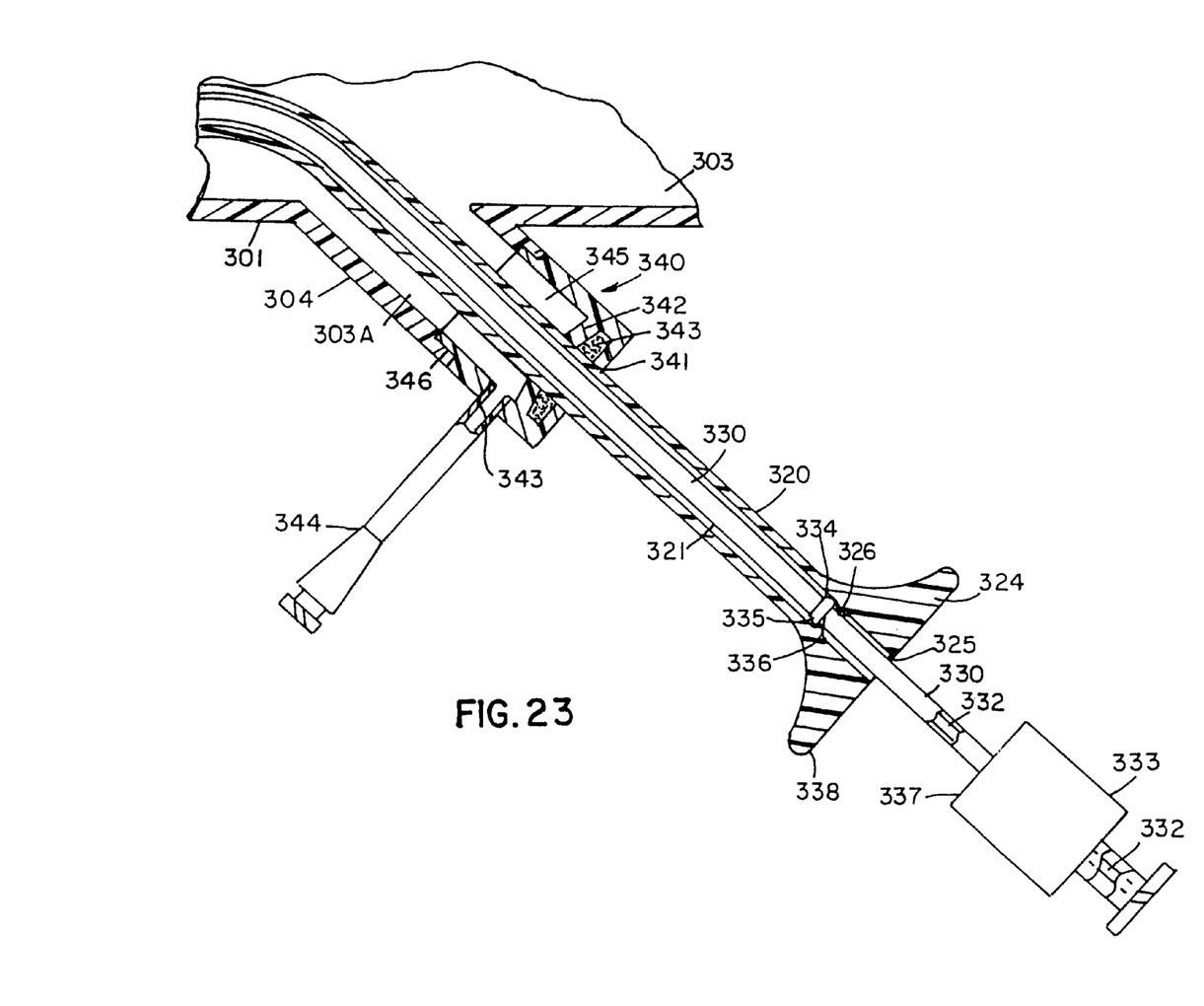
FIG. 23 is an enlarged sectional view of a portion of the instrument shown in FIG. 22.

In each of the embodiments of FIGS. 1 through 21 the operator that attaches to transverse members analogous to transverse member 315 constitutes a cable. In accordance with this invention the operator comprises an elongated sheath 320 having a central lumen 321. At its distal end, the sheath 320 carries two spaced anchors 322 and 323. The spacing between the anchors 322 and 323 corresponds to the axial extent of the transverse member 315. Thus when the portion of the sheath 320 between the anchors 322 and 323 sea s in the transverse member 315 thereby providing complimentary releasable engagement means, the anchors 322 and 323 lock the sheath axially to the transverse member 315. Any proximal or distal motion of the sheath 320 produces corresponding motion of the transverse member 315 and the piston 306. At its proximal end, the sheath 320 includes a handle 324. A lumen 325 through the handle 324 acts as an extension of the lumen 321. The lumen 325 is partially closed by a ring-like locking member 326 that may extend circumferentially around the interior of and radially into the lumen 325.

An elongated catheter 330 terminates in a needle portion 331 at its distal end. A lumen 332 extends through the catheter 330 and a standard injection hub 333 at the proximal end of the catheter 330. Thus it is possible for a physician to administer a sclerotherapy agent through the injection hub 333 to be dispensed through the needle 331. In addition the sclerotherapy needle 330 has an annularly extending collar 334 that serves as a complementary locking mechanism with the ring-like rib 326 on the sheath 320. During manufacture the sclerotherapy needle will be transferred through the lumen 321 by introducing the needle portion.331 into the lumen 325 and advancing the catheter 330 distally toward the anchor 322. As the collar 334 passes the circumferential rib 326, the rib 326 initially expands over a ramped outer surface 335. Once the collar 334 passes distally of the ring 326, a radial surface 336 on the ring 326 prevents the catheter 330 from being withdrawn.

In use for sclerotherapy the spring 314 holds the piston 307 distally with respect to the housing 306. The stop 323 and transverse member 315 prevent distal displacement of the elongated sheath 320. The injection hub 333 is withdrawn or moved proximally until the radial surface 336 of the collar 334 engages the ring 326 to define a stop, or motion limit, in the proximal direction. When the physician advances the sclerotherapy needle distally, a radial surface 337 on the injection hub 333 eventually engages a radial surface 338 of the handle 324 to stop, or limit, distal motion of the sclerotherapy needle 331 relative to the endoscope 300 and the elongated sheath 320. Consequently the distance between the radial surfaces 336 and 337 minus the axial distance between the ring 326 and surface 338 define the maximum displacement length of the sclerotherapy needle 331 with respect to the endoscope 300.

An instrument in accordance with this invention additionally includes a fitting 340 that attaches to the endoscope 300. The fitting 340 includes an opening or aperture 341 that aligns with the lumen 303A. A distally spaced inwardly protruding sealing gasket retaining structure 342 and the fitting carry a sealing gasket 343 interposed between the aperture 341 and the retaining structure 342. The gasket 343 provides a sliding seal that prevents any leakage when suction is applied or other fluids are administered through the working channel 303 and 303A. A side port 343 in the fitting 340 provides access for an infusion port 344 to communicate with a chamber 345 defined distally of the sealing gasket retaining 342. This allows the physician to apply suction for withdrawing a lesion into the distal end 302 of the instrument or to administer a flushing adjacent to the vicinity of the lesion through the working channel or lumen 303. FIG. 23 depicts a simple overlapped connection 346 between the fitting 340 and the port 304 for clarity. A threaded or similar releasable connection normally will be used.

In use, the system in an assembled form can be introduced from the proximal end 301 of the endoscope 300 through the working port 304. The fitting 340 then is affixed to the endoscope port 304. Typically, a physician or assistant first will affix the sheath 320 to the transverse member 315. Next the dispenser 305 is aligned with the working lumen 303 and attached to the distal end 302 of the endoscope 300. Normally the physician will position the endoscope 300 with the injection hub 333 withdrawn to its proximal limit thereby to withdraw the distal tip of the needle 331 to a position axially aligned with the end of the piston 307.

If upon visualization of a lesion the physician elects to dispense the ligating band 310, the physician first applies suction through the working lumen 303 by means of a standard suction port (not shown) on the endoscope 300. This suction pulls the lesion into the piston 307. Next the physician pulls the handle 324 proximally to withdraw the piston 307 and dispense the most distal of any of the ligating bands, such as ligating band 310, onto the lesion. When the physician releases the handle 324, the spring 314 advances the piston 307. Then any vacuum source applying the suction can be turned off while the physician attempts to visualize any additional lesions. If the physician decides sclerotherapy is the appropriate modality for the lesion, the physician can advance the infusion hub 333 thereby to inject the needle 331 into the lesion and apply an appropriate therapeutic agent through the infusion hub 333 and the needle 331 into the lesion. Then the physician can merely withdraw the infusion hub 333 until the collar 334 interferes with the circumferential ring 326 at the proximal stop position. If the physician determines that a single lesion should be treated with both a sclerotherapy agent and a ligating band, the apparatus of this invention allows both therapies to be used in sequence without relocating the endoscope.

Although this structure has been shown with respect to particular ligating instruments, it will be apparent that a dispenser or combination dispenser and sclerotherapy needle constructed in accordance with any of the disclosed embodiments is readily adapted for connection with introducers that can incorporate a wide variety of structures including those based upon rigid or flexible endoscopic structures. It will also be apparent that these instruments are reliable, readily producible and structurally sound. The use of a compression spring prevents premature dispensing of the ligating bands so that the requirement for the use of over tubes or separate stoppers is not required with ligating instruments incorporating this invention. Likewise, the use of the proximal and distal stops with the sclerotherapy needle establishes fixed limits on both proximal and distal positions.

In use the ligating instrument alone and in combination with the sclerotherapy needle is simple to use because it is merely necessary for the physician to position the ligating instrument and then move a trigger from one stop to another or advance the needle. There is no need for the physician to sense the amount of travel required for depositing a single ligating band or a single set of ligating bands or in advancing the needle.

Other structures for providing the reciprocal, definite motion of the piston member could be substituted for the spring and trigger operating mechanism. Other arrangements for holding the spring could be substituted to allow the dispenser to have a minimal length. This is particularly important when the dispenser attaches to an endoscopic device so that the dispenser does not unduly limit the field of view. Still other arrangements might be used to introduce the sclerotherapy needle as part of a combination involving a ligating band dispenser.

While this invention has been disclosed in terms of three particular embodiments and certain modifications, it will be apparent that many other modifications can be made to the specifically disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An instrument for selectively transferring a fluid and for dispensing ligature bands for band ligation, said instrument comprising:
   A. a ligature band dispenser adapted for coupling with a distal end of an endoscope and including first and second coaxially located segments for supporting a ligature band thereon and one of said segments being moveable between first and second positions relative to the other of said segments thereby to dispense the ligature band from the distal end of said instrument,
   B. an elongated sheath adapted for extension from the distal end of said instrument to a location exteriorly of said endoscope at a proximal end thereof through an endoscope working lumen, said sheath being adapted for attachment to said one segment and being slidable in the working lumen to operate said ligature band dispenser, and
   C. an elongated catheter extending through said elongated sheath to beyond the proximal and distal ends thereof and being slidable in said elongated sheath for defining a fluid transfer passage between the proximal and distal ends of said elongated catheter.

2. An instrument as recited in claim 1 wherein each of said one segment and said elongated sheath, at the distal end thereof, include a complementary, releasable engagement mechanism for releasably attaching said elongated sheath to said one segment.

3. An instrument as recited in claim 2 wherein said complementary, releasable engagement mechanism includes a notched fitting mounted on said one segment for capturing said elongated sheath in a transverse direction and a spaced anchor located on said elongated sheath at the distal end thereof for blocking axial motion of said elongated sheath with respect to said notched fitting.

4. An instrument as recited in claim 1 further comprising a plurality of elastic ligating bands, wherein said ligature band dispenser is adapted for positioning the plurality of the ligating bands at a plurality of lesions and wherein said one segment collectively supports a plurality of ligating bands at axially spaced positions thereon, said one segment being attached to said elongated sheath for movement therewith between proximal and distal positions to dispense one of the ligating bands from the distal end of said instrument.

5. An instrument as recited in claim 4 wherein said one segment includes a plurality of surfaces for supporting the ligating bands and said other segment includes a plurality of radial surfaces for engaging each ligating band during axial displacement of said one segment and wherein each of the plurality of surfaces is equal to the plurality of ligating bands.

6. An instrument as recited in claim 5 wherein said dispenser additionally includes a spring intermediate said segments for biasing said one segment distally with respect to said other segment.

7. An instrument as recited in claim 1 wherein said elongated sheath defines a sheath lumen and includes a handle for facilitating the movement of said elongated sheath in the working lumen, said handle including a lumen aligned with the sheath lumen for carrying said elongated catheter.

8. An instrument as recited in claim 7 wherein said catheter includes a hub at its proximal end for facilitating the transfer of fluid through said catheter, said hub and said handle coacting to define a distal stop that limits distal motion of said catheter with respect to said sheath.

9. An instrument as recited in claim 7 wherein said sheath and said catheter include first and second coacting mechanisms thereon respectively for establishing a proximal stop that limits proximal motion of said catheter with respect to said sheath.

10. An instrument as recited in claim 7 wherein said catheter includes a hub at its proximal end for facilitating the transfer of fluid through said catheter, said hub and said handle coacting to define a distal stop and wherein said sheath and said catheter include first and second coacting mechanisms thereon respectively for establishing a proximal stop, said proximal and distal stops limiting, respectively, the proximal and distal motion of said catheter with respect to said sheath.

11. An instrument as recited in claim 7, said endoscope including an endoscope port for direct access to the working lumen, said instrument additionally including a fitting for attachment to the endoscope port, said fitting including a fitting port for establishing a passage to the working lumen and a sliding seal spaced from said fitting port for closing said fitting around said elongated sheath whereby said elongated sheath can slide in the working lumen through said fitting.

12. An instrument as recited in claim 7 wherein said sheath includes an axially spaced anchor located at the distal end thereof and said one segment includes a segment engagement mechanism for engaging said sheath intermediate said anchor.

13. An instrument for selectively transferring a sclerotherapy agent to a lesion or dispensing one of a plurality of ligature bands onto the lesion, said instrument comprising:

A. a ligature band dispenser connecting to a distal end of an endoscope and including a coaxially located piston and housing that support the plurality of ligating bands thereon, said housing attaching to the distal end of the endoscope and said piston being moveable between first and second positions relative to said housing thereby to dispense one ligating band from the distal end of said instrument, B. an elongated sheath adapted for extension between the distal end of said instrument to a location exteriorly of said endoscope at a proximal end thereof through an endoscope working lumen, said sheath being attached to said piston and being slidable in the working lumen to operate said dispenser, and C. an elongated catheter extending through said elongated sheath to beyond the proximal and distal ends thereof and being slidable in said elongated sheath, said catheter terminating in a needle portion at its distal end for administering a sclerotherapy agent to a lesion.

14. An instrument as recited in claim 13 including a notched fitting mounted on said piston for capturing said elongated sheath in a transverse direction and spaced anchors on said elongated sheath at the distal end thereof for blocking axial motion of said elongated sheath with respect to said notched fitting.

15. An instrument as recited in claim 13 wherein said piston includes a plurality of surfaces for supporting the ligating bands and said housing includes a plurality of radial surfaces for engaging each ligating band during axial displacement of said piston and wherein each of the plurality of surfaces is equal to the plurality of ligating bands.

16. An instrument as recited in claim 15 wherein said dispenser includes a spring intermediate said piston and housing that biases said piston distally with respect to said housing.

17. An instrument as recited in claim 13 wherein said elongated sheath includes a sheath lumen and a handle for facilitating the movement of said elongated sheath in the working lumen, said handle including a lumen aligned with the sheath lumen for carrying said elongated catheter.

18. An instrument as recited in claim 17 wherein said catheter includes a hub at its proximal end for facilitating the transfer of fluid through said catheter, said hub and handle coacting to define a distal stop that limits distal motion of said catheter with respect to said sheath.

19. An instrument as recited in claim 17 wherein said sheath and said catheter include a coacting ring and collar respectively that establish a proximal stop that limits proximal motion of said catheter with respect to said sheath.

20. An instrument as recited in claim 13, said endoscope including an endoscope port for direct access to the working lumen, said instrument additionally including a fitting that attaches to the endoscope port, said fitting including a fitting port for establishing a passage to the working lumen and a sliding seal for providing a sliding seal around said elongated sheath when said elongated sheath slides in the working lumen through said fitting.

* * * * *